United States Patent [19]

O'Neill et al.

[11] Patent Number: 5,461,075

[45] Date of Patent: Oct. 24, 1995

[54] USE OF VANILLOIDS FOR THE PREVENTION OF LESIONS DUE TO HERPES SIMPLEX INFECTIONS

[75] Inventors: Timothy P. O'Neill; Gerald B. Kasting, both of Wyoming; Thomas L. Cupps, Oxford, all of Ohio

[73] Assignee: The Procter & Gamble Company, Cincinnati, Ohio

[21] Appl. No.: 670,373

[22] Filed: Mar. 14, 1991

Related U.S. Application Data

[63] Continuation of Ser. No. 404,705, Sep. 8, 1989, abandoned, which is a continuation-in-part of Ser. No. 358,751, Jun. 2, 1989, abandoned, which is a continuation-in-part of Ser. No. 208,321, Jun. 17, 1988, abandoned.

[51] Int. Cl.$^6$ ................................. A61K 31/165
[52] U.S. Cl. ................. 514/617; 514/622; 514/620; 514/621; 514/618
[58] Field of Search .................... 514/617, 622, 514/620, 621, 618

[56] References Cited

U.S. PATENT DOCUMENTS

| | | | |
|---|---|---|---|
| 4,238,508 | 12/1980 | Nelson | 424/324 |
| 4,313,958 | 2/1982 | LaHann | 424/324 |
| 4,401,663 | 8/1983 | Buckwalter et al. | 424/321 |
| 4,424,205 | 1/1984 | LaHann et al. | 424/72 |
| 4,443,473 | 4/1984 | Buckwalter et al. | 424/300 |
| 4,460,602 | 7/1984 | Buckwalter et al. | 424/322 |
| 4,493,848 | 1/1985 | LaHann et al. | 424/324 |
| 4,532,139 | 7/1985 | Janusz et al. | 514/627 |
| 4,536,404 | 8/1985 | Bernstein | 514/627 |
| 4,544,668 | 10/1985 | Janusz et al. | 514/563 |
| 4,544,669 | 10/1985 | LaHann et al. | 514/563 |
| 4,564,633 | 1/1986 | LaHann et al. | 514/538 |
| 4,810,716 | 3/1989 | Connor et al. | 514/365 |

FOREIGN PATENT DOCUMENTS

| | | | |
|---|---|---|---|
| 0068590 | 1/1983 | European Pat. Off. | C07C 127/17 |
| 0089710 | 9/1983 | European Pat. Off. | C07C 103/76 |
| 0187009 | 7/1986 | European Pat. Off. | C07C 103/60 |
| 0206609 | 12/1986 | European Pat. Off. | C07C 103/30 |
| 0282127 | 9/1988 | European Pat. Off. | C07C 103/38 |
| 0347000 | 12/1989 | European Pat. Off. | A61K 31/165 |
| 2168976 | 7/1986 | United Kingdom | C07C 103/38 |
| 2168975 | 7/1986 | United Kingdom | C07C 103/78 |
| 2168974 | 7/1986 | United Kingdom | C07C 69/732 |
| 2206347 | 1/1989 | United Kingdom | C07C 157/07 |
| WO89/04297 | 5/1989 | WIPO | C07C 103/38 |

OTHER PUBLICATIONS

Yaksh et al., "Intrathecal Capsaicin Depletes Substance P in the Rat Spinal Cord and Produces Prolonged Thermal Analgesia", Science, vol. 206, pp. 481–483 (1979).

Bernstein, J. E., "Capsaicin in the Treatment of Dermatologic Disease", Cutis, vol. 30, pp. 352–353, (Apr. 1987).

Handwerker et al., "C–Fibre Functions After Topical Application of Capsaicin to a Peripheral Nerve and after Neonatal Capsaicin Treatment", Antidromic Vasodilation and Neurogenic Inflammation: Satellite Symposium of the 29th International Congress of Physiological Sciences, Newcastle, Australia, 1983, Edited by Chahl, L. A., Szolcsanyi, J. and F. Lembeck, Akademiai Kiado, Budapest, pp. 57–78, (1984).

Ljungdahl et al., "Herpes Simplex Virus Infection in Capsaicin–Treated Mice", Journal of Neurological Sciences, vol. 72, pp. 223–230, (1986).

Taylor et al., "The Effect of Capsaicin on Axoplasmic Transport in a Rat Peripheral Nerve", Antidromic Vasodilation and Neurogenic Inflammation: Satellite Symposium of the 29th International Congress of Physiological Sciences, Newcastle, Australia, 1983, Edited by Chahl, L. A., Szolcsanyi, J. and F. Lembeck, Akademiai Kiado, Budapest, pp. 165–171, (1984).

Bernstein et al., "Treatment of Chronic Postherpetic Neuralgia with Topical Capsaicin", Journal of the American Academy of Dermatology, vol. 17, pp. 93–96, (1981).

Jancso et al., "The Modulation of Cutaneous Inflammatory Reactions by Peptide–Containing Sensory Nerves", International Journal of Tissue Reactions, vol. VIII, pp. 449–457, (1985).

Jansco et al., "Impairment of Axon Reflex Vasodilatation after Herpes Zoster", Clinical and Experimental Dermatology, vol. 8, pp. 27–31, (1983).

"A Herpes Therapy Too Hot to Take?", Science, vol. 246 (1989), p. 1385.

Alving, K., R. Matran, J. S. Lacroix and J. M. Lundberg, "Allergen Challenge Induces Vasodilatation in Pig Bronchial Circulation via a Capsaicin–Sensitive Mechanism", Acta Physiol Scand, vol. 134 (1988), pp. 571–572.

Arvier, P. T., L. A. Chahl & R. J. Ladd, "Modification by Capsaicin and Compound 48/80 of Dye Leakage Induced by Irritants in the Rat", Br. J. Pharmac., vol. 59 (1977), pp. 61–68.

Gamse, R., A. Saria, J. M. Lundberg & E. Theodorsson–Norheim, "Behavioral and Neurochemical Changes After Intracisternal Capsaicin Treatment of the Guinea Pig", Neuroscience Letters, vol. 64 (1986), pp. 287–292.

Geppetti, P., B. M. Fusco, S. Marabini, C. A. Maggi, M. Fanciullacci & F. Sicuteri, "Secretion, Pain and Sneezing Induced by the Application of Capsaicin to the Nasal Mucosa in Man", Br. J. Pharmacol., vol. 93 (1988), pp. 509–514.

Herbort, C. P., S. S. Weissman & D. G. Payan, "Role of Peptidergic Neurons in Ocular Herpes Simplex Infection in Mice", The FASEB Journal, vol. 3 (Nov. 1989), pp. 2537–2541.

Jansco, G., E. Kiraly, "Sensory Neurotoxins: Chemically Induced Selective Destruction of Primary Sensory Neurons", Brain Research, vol. 210 (1981), pp. 83–89.

(List continued on next page.)

Primary Examiner—Marianne M. Cintins
Assistant Examiner—Russell Travers
Attorney, Agent, or Firm—Milton B. Graff; David L. Suter

[57] ABSTRACT

The present invention provides methods of preventing lesions due to herpes simplex infections in humans and lower animals by treatment with natural and synthetic vanilloid compounds.

23 Claims, No Drawings

OTHER PUBLICATIONS

Jansco, N. A. Jansco–Gabor & J. Szolcsanyi, "Direct Evidence for Neurogenic Inflammation and Its Prevention by Denervation and By Pretreatment with Capsaicin", Br. J. Pharmac. Chemother., vol. 31 (1967), pp. 138–151.

Jansco, G., E. Kiraly & A. Jansco–Gabor, "Pharmacologically Induced Selective Degeneration of Chemosensitive Primary Sensory Neurones", Nature, vol. 270, No. 22/29 (1977), pp. 741–743.

Jansco, G. and B. Lynn, "Possible Use of Capsaicin in Pain Therpy", Clin J. Pain, vol. 3 (1987), pp. 123–126.

Jones, E. C. S. & F. L. Pyman, "The Relation Between Chemical Constitution and Pungency in Acid Amides", J. Chem. Soc., vol. 127 (1925), pp. 2588–2598.

Kiernan, J. A., "A Study of Chemically Induced Acute Inflammation in the Skin of the Rat", Quarterly Journal of Experimental Physiology, vol. 62 (1977), pp. 151–161.

LaMotte, R. H., D. A. Simone, T. K. Baumann, C. N. Shain & M. Alreja, "Hypothesis for Novel Classes of Chemoreceptors Mediating Chemogenic Pain and Itch." In: Pain Research and Clinical Management, vol. 3; Proceedings of the Vth World Congress on Pain, R. Dubner, G. F. Gebhart & M. R. Bonds (eds.), Elsevier Science Publishers, (1988), pp. 529–535.

Lundblad, L., A. Anggard & J. M. Lundberg, "Effects of Antidromic Trigeminal Nerve Stimulation in Relation to Parasympathetic Vasodilation in Cat Nasal Mucosa", Acta Physiol Scand, vol. 119 (1983), pp. 7–13.

Lundblad, L., A. Saria, J. M. Lundberg & A. Anggard, "Increased Vascular Permeability in Rat Mucosa Induced by Substance P and Stimulation of Capsaicin–Sensitive Trigeminal Neurons", Acta Otolaryngol, vol. 96 (1983), pp. 479–484.

Lundblad, L. & J. M. Lundberg, "Capsaicin Sensitive Sensory Neurons Mediate the Response to Nasal Irritation Induced by the Vapour Phase of Cigarette Smoke", Toxicology, vol. 33 (1984), pp. 1–7.

Lundblad, L., J. M. Lundberg, A. Anggard & O. Zetterstrom, "Capsaicin–Sensitive Nerves and the Cutaneous Allergy Reaction in Man", Allergy, vol. 42 (1987), pp. 20–25.

Lundblad, L., X–Y Hua & J. M. Lundberg, "Mechanisms for Reflexive Hypertension Induced by Local Application of Capsaicin and Nicotine to the Nasal Mucosa", Acta Physiol Scand, vol. 121 (1984), pp. 277–282.

Lundblad, L., "Protective Reflexes and Vascular Effects in the Nasal Mucosa Elicited by Activation of Capsaicin–Sensitive Substance P–Immunoreactive Trigeminal Neurons", Acta Physiologica Scandinavica, Sup. 529 (1984), pp. 1–42.

Lundblad, L., J. M. Lundberg, E. Brodin & A. Anggard, "Origin and Distribution of Capsaicin–Sensitive Substance P–Immunoreactive Nerves in the Nasal Mucosa", Acta Otolaryngol, vol. 96 (1983), pp. 485–493.

Lundblad, L., J. M. Lundberg & A. Anggard, "Local and Systemic Capsaicin Pretreatment Inhibits Sneezing and the Increase in Nasal Vascular Permeability Induced by Certain Chemical Irritants", Naunyn–Scimiedeberg's Arch Pharmacol, vol. 326 (1984), pp. 254–261.

Lundblad, L., E. Brodin, J. M. Lundberg & A. Anggard, "Effects of Nasal Capsaicin Pretreatment and Cryosurgery on Sneezing Reflexes, Neurogenic Plasma Extravasation, Sensory and Sympathetic Neurons", Acta Otolaryngol (Stockh), vol. 100 (1985), pp. 117–127.

Marabini, S., G. Ciabatti, G. Polli, B. M. Fusco, P. Geppetti, C. A. Maggi, M. Fanciullacci & F. Sicuteri, "Effect of Topical Nasal Treatment with Capsaicin in Vasomotor Rhinitis", Regulatory Peptides, vol. 22 (1988), p. 121.

Mizoguchi, H. & R. Hicks, "Effect of Neurokinins on Vascular Permeability in Guinea Pigs", The FASEB Journal, Apr., 1987 (Abstract only).

Newmann, A. A., "Natural and Synthetic Pepper–Flavoured Substances", Chemical Products, (Mar., 1954), pp. 102–106.

Saria, A., & G. Wolf, "Beneficial Effect of Topically Applied Capsaicin in the Treatment of Hyperreactive Rhinopathy", Reg. Peptides, vol. 22 (1988), p. 167.

Shimura, S., S. Sasaki, H. Okayama, H. Sasaki & T. Takishima, "Effect of Substance P on Mucus Secretion of Isolated Submucosal Gland from Feline Trachea", J. Appl. Physiol., vol. 63, No. 2 (1987), pp. 646–653.

Stanberry, L. R., "Capsaicin Interferes with Anterograde Neural Spread of Virus in Primary and Recurrent Genital Herpes", 14th International Herpesvirus Workshop, Nyborg Strand, Denmark, 1989 (Abstract only).

Szeki, T., "Contributions Towards Understanding the Relation Between the Chemical Constitution and the Sharp Taste of Acylamines", Arch. Pharm., vol. 268 (1930), pp. 151–157.

Szolcsanyi, J. & A. Jansco–Gabor, "Sensory Effects of Capsaicin Congeners, I. Relationship between chemical structure and pain–producing potency of pungent agents", Arzneim–Forsch., vol. 25 (1975), pp. 1877–1880.

Szolcsanyi, J. & A. Jansco–Gabor, "Sensory Effects of Capsaicin Congeners, II. Importance of chemical structure and pungency in desensitizing activity of capsaicin–type compounds", Arzneim–Forsch., vol. 26, No. 1 (1976), pp. 33–37.

Toth–Kasa, I., G. Jansco, A. Bognar, S. Husz & F. Obal, Jr., "Capsaicin Prevents Histamine–Induced Itching", Int. J. Clin. Pharm. Res., vol. VI, No. 2 (1986), pp. 163–169.

Virus, R. M. & G. F. Gebhart, "Pharmacologic Actions of Capsaicin: Apparent Involvement of Substance P and Serotonin", Life Sciences, vol. 25 (1979), pp. 1273–1284.

Watson, C. P. N., R. J. Evans & V. R. Watt, "Post–Herpetic Neuralgia and Topical Capsaicin", Pain, vol. 33 (1988), pp. 333–340.

Winning, A. J., R. D. Hamilton, S. A. Shea & A. Guz, "Respiratory and Cardiovascular Effects of Central and Peripheral Intravenous Injections of Capsaicin in Man: Evidence for Pulmonary Chemosensitivity", Clin. Sci., vol. 71 (1986), pp. 512–529.

Harbour et al, "Recurrent Herpes Simplex in the Mouse: Inflammation in the Skin and Activation of Virus in the Ganglia Following Peripheral Stimulation", *Journal of General Virology*, vol. 64, pp. 1491–1498, (1983).

USE OF VANILLOIDS FOR THE PREVENTION OF LESIONS DUE TO HERPES SIMPLEX INFECTIONS

This is a continuation of application Ser. No. 404,705, filed on Sep. 8, 1989, now abandoned, which is a Continuation-in-Part of application Ser. No. 358,751, filed Jun. 2, 1989, now abandoned, which is a Continuation-in-Part of application Ser. No. 208,321, filed Jun. 17,1988, now abandoned.

TECHNICAL FIELD

This application relates to the use of vanilloid compounds for the treatment or prevention of Lesions of herpes simplex infections.

BACKGROUND OF THE INVENTION

The present invention involves a novel use for natural and synthetic vanilloid compounds. The following are non-limiting examples of such vanilloid compounds, and references in which they are disclosed; all of the following references are hereby incorporated herein in their entirety by reference: capsaicin (trans-8-methyl-N-vanillyl-6-nonenamide) and "synthetic" capsaicin (N-vanillylnonanamide) in U.S. Pat. No. 4,313,958, LaHann, issued Feb. 2, 1982; capsaicin in Yaksh, et al, *Science,* 206, pp 481–483 (1979); capsaicin in Jancso, et al, *Naunyn-Schmiedeberg's Arch. Pharmacol.,* Vol. 311, pp 285–288 (1980); capsaicin in Holzer et al, *Eur. J. Pharm.* Vol. 58, pp. 511–514 (1979); 3-hydroxyacetanilide in U.S. Pat. No. 4,238,508, Nelson, issued Dec. 9, 1980; hydroxyphenylacetamides in European Patent Application 0089710, LaHann, et al, published Sep. 28, 1983; N-vanillyl sulfonamides in U.S. Pat. No. 4,401,663, Buckwalter, et al, issued Aug. 30, 1983; hydroxyphenyl-acetamides in U.S. Pat. No. 4,424,205, LaHann, et al, issued Jan. 31, 1984; N-(3- or 4-hydroxy or 3,4-dihydroxybenzyl) carbamates in U.S. Pat. No. 4,443,473, Buckwalter, et al, issued Apr. 17, 1984; N-[(substituted phenyl) methyl]-cis-monounsaturated alkenamides in U.S. Pat. No. 4,493,848, LaHann, et al, issued Jan. 15, 1985; N-(3-methoxy-4-hydroxybenzyl and phenyl) ureas and thioureas in U.S. Pat. No. 4,460,602, Buckwalter, et al, issued Jul. 17, 1984; N-vanillylureas in European Patent Application 0068590, Buckwalter, et al, published Jan. 5, 1983; N-[(substituted phenyl)methyl]alkynamides in U.S. Pat. No. 4,532,139, Janusz, et al, issued Jul. 30, 1985; methylene substituted N-[(substituted phenyl)methyl]alkanamides in U.S. Pat. No. 4,544,668, Janusz, et al, issued Oct. 1, 1985; N-[(substituted phenyl)methyl]-diunsaturated amides in U.S. Pat. No. 4,544,669, LaHann, et al, issued Oct. 1, 1985; monoalkenamides in U.S. Pat. No. 4,564,633, LaHann, et al, issued Jan. 14, 1986; substituted phenylacetic acid esters in British Patent Specification 2,168,974, Loomans, et al, published Jul. 2, 1986; N-(substituted alkyl)alkanamides and thioamides in British Patent Specification 2,168,976, Loomans, et al, published Jul. 2, 1986; substituted aromatic-araalkanamides in British Patent Specification 2,168,975, Janusz et al, published Jul. 2, 1986; and beta-aminoethyl-substituted phenyl compounds in European Patent Application No. 282,127, Gardner, et al., published Sep. 14, 1988.

Vanilloid compounds have been generally disclosed in the above references to have analgesic, anti-irritant and anti-inflammatory activity.

The use of capsaicin to affect the nervous system of humans and other animals, and to treat the pain associated with herpes zoster infections, has been disclosed in a number of references. Handwerker, H. O., U. Holzer-Petsche, Ch. Heym and E. Welk, "C-Fibre Functions After Topical Application of Capsaicin to a Peripheral Nerve and after Neonatal Capsaicin Treatment", *Antidromic Vasodilation and Neurogenic Inflammation: Satellite Symposium of the* 29th *International Congress of Physiological Sciences,* Newcastle, Australia, 1983, Edited by Chahl, L. A., J. Szolcsanyi, and F. Lembeck, Akademiai Kiado, Budapest, (1984) pp. 57–78, discloses that after repeated capsaicin application, nociceptors become desensitized to subsequent chemical and presumably also heat stimuli. Taylor, D. C. M., Fr.-K. Pierau and J. Szolcsanyi, "The Effect of Capsaicin on Axoplasmic Transport in a Rat Peripheral Nerve", *Antidromic Vasodilation and Neurogenic Inflammation: Satellite Symposium of the* 29th *International Congress of Physiological Sciences,* Newcastle, AUstralia, 1983, Edited by Chahl, L. A., Szolcsanyi, J. and F. Lembeck, Akademiai Kiado, Budapest, (1984), pp. 165–171, discloses that systemic capsaicin decreased substance P levels in the dorsal root ganglia and the spinal cord, and that nerve growth factor (NGF) transport in the peripheral nerve may be blocked by systemic capsaicin. Jancso, G., F. Obal, Jr., I. Toth-Kasa, M. Katona and S. Husz, "The Modulation of Cutaneous Inflammatory Reactions by Peptide-Containing Sensory Nerves", *International Journal of Tissue Reactions,* Vol. VII, (1985), pp. 449–457, discloses a possible role of the nervous system to the mechanisms of inflammation through peptide containing sensory nerves. While rats treated neonatally with capsaicin showed complete abolishment of neuro-genic inflammation, repeated topical application of the skin with capsaicin (local desensitization) abolished the neurogenic inflammatory response for several days, along with strongly reduced chemical pain sensitivity and elevated thresholds for warmth and heat pain sensations. Local capsaicin desensitization of the skin prevented whealing, flare and itch in patients with acquired cold and heat urticaria. Jancso, G., S. Husz and N. Simon, "Impairment of Axon Reflex Vasodilatation after Herpes Zoster", *Clinical and Experimental Dermatology,* Vol. 8, (1983), pp. 27–31, discloses an effect on chemosensitive primary sensory neurons and impairment of axon reflex vasodilatation in skin vessels following herpes zoster infection and the possible mechanisms by which herpes zoster may effect the vascular reactions of the skin.

Capsaicin has been disclosed as an effective compound for the treatment of severe pain associated with herpes zoster infections. Bernstein, J. E., "Capsaicin in the Treatment of Dermatologic Disease", Cutis, Vol. 39, (April 1987), pp. 352–353, discloses use of capsaicin in the possible treatment of post-herpetic neuralgia and psoriasis. Bernstein, J. E., D. R. Bickers, M. V. Dahl, Jay Y. Roshal, "Treatment of Chronic Postherpetic Neuralgia with Topical Capsaicin", *Journal of the American Academy of Dermatoloqy,* Vol. 17, (1981), pp. 93–96, discloses topical application of capsaicin to patients suffering from postherpetic neuralgia as a possible approach for alleviating postherpetic neuralgia and other syndromes characterized by severe localized pain. U.S. Pat. No. 4,536,404, Bernstein, issued Aug. 20, 1985, discloses a method for treating post-herpetic neuralgia due to herpes zoster wherein an effective amount of capsaicin is topically applied to the area affected with herpes zoster to relieve the symptoms of post-herpetic neuralgia.

Capsaicin's effect on the neurogenic response on the skin and in sensory transmission in mice with herpes simplex infections is disclosed in the following two references. Harbour, D. A., T. J. Hill and W. A. Blyth, "Recurrent Herpes Simplex in the Mouse: Inflammation in the Skin and Activation of Virus in the Ganglia Following Peripheral Stimulation", *Journal of General Virology*, Vol. 64, (1983), pp. 1491–1498, discloses chemical stimuli to the skin which induce recurrent herpes simplex virus disease and reactivation of infectious virus in the ganglia. Capsaicin is injected subcutaneously prior to injection of the mice with dye to help determine the effect of mediators on the permeability of blood vessels. Ljungdahl, A., K. Kristensson, J. M. Lundberg, E. Lycke, B. Svennerholm and R. Ziegler, "Herpes Simplex Virus Infection in Capsaicin-Treated Mice", *Journal of the Neurological Sciences*, Vol. 72, (1986), pp. 223–230, discloses that capsaicin injected subcutaneously prior to herpes simplex virus (HSV) inoculation of the snouts of four day old (neonatal) mice, reduced the mortality rate of HSV-infected mice.

Herpes Zoster Infections

Herpes zoster infections are caused by the varicella-zoster virus (VZV), the etiologic agent of the conditions commonly known as shingles, zona and acute posterior ganglionitis.

VZV infections usually cause severe pain and exhibit large groups of lesions distributed along the course of a sensory nerve. Vesicular eruption causes neuralgic pain in the cutaneous area supplied by the peripheral sensory nerves. The vesicular eruptions of herpes zoster are often activated by local lesions involving the posterior root ganglia, systemic diseases such as Hodgkins, and immunosuppressive therapy.

VZV is also the causative agent in chicken pox. Later herpes zoster infections (or shingles outbreaks) are most common after the age of fifty. Crops of vesicles form on an erythematous base and follow the sensory distribution of one or more posterior root ganglia. The sensory zone on the skin that is affected is usually hyperaesthetic with associated severe pain.

Postherpetic neuralgia is often seen in patients over 60 years of age following a vesicular eruption caused by VZV. Following the eruption, a syndrome of dermatologic rash and pain usually ensues. The rash generally resolves spontaneously in 2 to 3 weeks. The pain may continue and be severe. The treatment of postherpetic neuralgia has often been unsatisfactory and is essentially symptomatic, often requiring potent analgesics and tranquilizers. The postherpetic neuralgia associated with VZV infections may persist for months or years. The pain can be so intractable that it has been implicated in prolonged depression and even suicide. Not infrequently the pain is sufficiently severe and persistent that neurosurgical procedures may be employed in an effort to relieve the patient's discomfort.

Herpes zoster infections rarely recur in a patient (recurrence rate is less than 2%); one attack, generally associated with an outbreak of lesions in any one of numerous areas of the skin surface, usually confers immunity.

HERPES SIMPLEX INFECTIONS

Clinically, herpes zoster infections may have some similarity to herpes simplex virus (HSV) infections, but several important differences between the two exist.

Herpes simplex lesions are characterized by generalized or localized cutaneous and mucosal lesions, often with associated severe constitutional (general, not local) symptoms. Following an acute primary skin infection, the virus spreads along sensory nerves and becomes established in the regional sensory ganglia, or area of neuron cell bodies. HSV usually present with latent infections in the trigeminal or presacral ganglia. Although VZV infections generally produce latent infections, these occur mainly in the dorsal root ganglia.

HSV infections are generally of two types, Type I or Type II. Type I HSV infections are mainly implicated in oral or ocular herpes infections. HSV Type II infections are usually genital and transmitted primarily through direct contact with herpes lesions. While herpes simplex lesions may appear anywhere on the skin or mucosa, they most frequently appear on the mouth, the lips, the conjunctiva and cornea and the genitalia.

Unlike the 2% recurrence rate of VZV infections, the likelihood of Type I HSV recurrence is 80%, while the likelihood of Type II HSV recurrence is 50%. Reinfection with different strains of Type II HSV may also occur. Recurrent herpetic eruptions can be precipitated by conditions as broad as over exposure to sunlight, febrile illness, physical or emotional stress, or certain foods or drugs.

Postherpetic neuralgia is not generally seen with HSV infections. The primary lesions of HSV (vesicular eruptions) are the most painful, prolonged and widespread. During periods of vesicular eruption, patients often experience pain in the region of viral infection. This pain, though it may be severe, resolves upon healing of the herpetic lesions, and unlike VZV infections, leaves the patient basically asymptomatic between recurrent herpetic episodes. Treatment regimes for recurrent HSV infections have shown little promise in preventing herpes lesions, though there has been some relief of pain and other symptoms.

OBJECTS OF THE PRESENT INVENTION

It is an object of the present invention to provide new methods which are effective for treating or preventing herpes simplex Type I and Type II infections and the attendant recurrent discomfort, lesions and pain.

It is a further object of the present invention to provide methods for topical treatments to resolve many of the symptoms associated with herpes simplex infections; especially those associated with herpes Type II infections.

It is a still further object of the present invention to provide such methods of treatment which produce analgesia without the loss of mechanical sensation (i.e., "numbing") or motor coordination.

It is a still further object of the present invention to provide methods for treating or preventing genital herpes simplex infections and the attendant recurrent discomfort, lesions, and pain (especially herpes simplex Type II infections).

SUMMARY OF THE INVENTION

The present invention provides methods of treating or preventing lesions of herpes simplex infections in humans and lower animals by treatment with natural and synthetic vanilloid compounds, and the pharmaceutically-acceptable salts thereof.

This invention particularly relates to methods of treatment whereby pharmaceutical compositions containing said natural and synthetic vanilloid compounds are topically applied to prevent the recurrence of herpes simplex Type I or Type II lesions.

DETAILED DESCRIPTION OF THE INVENTION

The term "alkyl", as used herein, means carbon-containing chains which may be straight, branched, or cyclic; substituted or unsubstituted; and which may be saturated, monounsaturated (i.e., one double or triple bond in the chain), or polyunsaturated (e.g., two or more double bonds in the chain; two or more triple bonds in the chain; one or more double and one or more triple bonds in the chain). Unless indicated otherwise, alkyl are preferably as follows. Preferred alkyl are straight or branched chain, especially straight chain. Preferred alkyl are unsubstituted. Preferred alkyl are monounsaturated, or especially saturated. Preferred alkyl are $C_1$–$C_{20}$, more preferably $C_1$–$C_{10}$, more preferably still $C_1$–$C_6$, still more preferably $C_1$–$C_4$, most preferably $C_1$–$C_2$, especially $C_1$.

The term "carboxylate", as used herein, means an organic carboxylic acid moiety (i.e., —$CO_2H$), and the salts (e.g., sodium; potassium; calcium; tetraethylammonium) and esters (e.g., methyl ester; ethyl ester) and amides (e.g., unsubstituted amide; N-methylamide; N,N-dimethylamide) thereof which are acceptable from a toxicity viewpoint for administration to humans or lower animals.

The terms "aryl" and "heteroaryl", as used herein, mean aryl or heteroaryl rings which may be mono-, di-, or tri-substituted or unsubstituted, preferably monosubstituted or unsubstituted. Additionally, heteroaryl rings comprise at least one oxygen, sulfur or nitrogen atom in the ring structure. Preferred aryls and heteroaryl s include substituted or unsubstituted phenyl, naphthyl, pyridyl, pyrimidyl, imidazolyl, furanyl, thiophenyl, pyrazolyl, triazolyl, tetrazolyl, thiazolyl, triazinyl, pyrrolyl, indolyl and purinyl. More preferred aryls and heteroaryls include unsubstituted and substituted phenyl, pyridyl, imidazolyl, furanyl and thiophenyl. Most preferred aryl is unsubstituted or substituted phenyl. Preferred substituents include halogen, hydroxy, $C_1$–$C_{16}$ alkoxy, amino, nitro, cyano, phenyl, benzyl, benzyloxy, trifluoromethyl, formylamino, carboxylate and $C_1$–$C_6$ alkyl. More preferred aryl or heteroaryl is unsubstituted.

The term "substituted", as used herein for alkyl and aryl groups, means alkyl or aryl groups that can be mono- or polysubstituted. Preferred is mono-, di- or trisubstituted; more preferred is monosubstituted. Preferred substitutents are selected from the group consisting of halogen, hydroxy, amino, nitro, cyano, trifluoromethyl, thiol, aryl, alkyl, carboxylate and OR wherein R is aryl or an unsubstituted alkyl group (especially methoxy and ethoxy).

The term "carboxylate", as used herein, means an organic carboxyl ic acid moiety (i.e., COOH), and the salts (e.g., sodium, potassium, calcium, tetraethylammonium) and esters (e.g., methyl ester, ethyl ester) and amides (e.g., unsubstituted amide, N-methyl amide, N,N-dimethyl amide) thereof.

As used herein, saturated alkyl groups are referred to as "alkanyl"; unsaturated alkyl groups comprising double bonds in the chain are referred to as "alkenyl" (preferred are chains having the double bonds in the "Z" or "cis" geometric configuration); and unsaturated alkyl groups comprising triple bonds in the chain are referred to as "alkynyl". The designation of geometric configurations for any double bonds present in compounds of the present invention utilizes the art-known nomenclature "Z" and "E", and is fully described in Morrison and Boyd, *Organic Chemistry*, Third Edition (Allyn and Bacon, Inc., Boston; 1973), pp. 131–133 and 148–151; and March, *Advanced Organic Chemistry*, Second Edition (McGraw-Hill Book Company, New York; 1977), pp. 86–124; the disclosures of both these references being incorporated herein by reference in their entirety.

The compounds useful in the present invention are natural and synthetic vanilloid compounds, and the pharmaceutically-acceptable salts thereof, having the general structure:

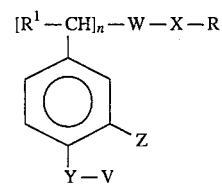

In structure (1) n=0 or 1.

In structure (1), the —W—X— moiety is selected from —C(O)NH—, —C(S)NH—, —S(O)$_2$NH—, —NHC(O)O—, —NHC(S)O—, —NHC(O)NH—, and —NHC(S)NH—. Preferred —W—X— is selected from —C(O)NH—, —C(S)NH—, —NHC(O)NH—, —NHC(S)NH— and —S(O)$_2$NH—. More preferred —W—X— is selected from —C(O)NH—, —C(S)NH—, and —NHC(O)NH—. Most preferred —W—X— is —C(O)NH—. Either available bond of the —W—X— moiety may be bonded to the —R moiety, with the other bond being attached to the benzyl carbon atom, or directly attached to the benzene ring.

In structure (1), the —$R^1$ moiety is selected from hydrogen, hydroxy, alkyl esters of hydroxy having from about 1 to about 5 carbon atoms, alkyl having from about 1 to about 5 carbon atoms, and alkoxy having from about 1 to about 5 carbon atoms. Preferred —$R^1$ is selected from hydrogen, hydroxy, and methyl; most preferred —$R^1$ is hydrogen.

In structure (1), the —Z moiety is selected from hydrogen, hydroxy and methoxy; preferred —Z is selected from hydroxy and methoxy. Most preferred —Z is methoxy.

In structure (1), the —Y— moiety is selected from —O—, —S—, —$NR^4$—, —OC(O)—, —OSO$_3^-$—, and —OPO$_3^=$—, where —$R^4$ is selected from hydrogen and $C_1$–$C_4$ alkanyl; preferred —Y— is selected from —O—, —S— and —NH—. More preferred —Y— is selected from —O— and —S—; most preferred —Y— is —O—.

In structure (1) the —V moiety is selected from hydrogen, short chain alkyl, and —$CR^2_2$—$CR^2_2$—$NH_2$. Preferred —V is selected from $C_1$ to $C_3$ alkyl and hydrogen. Even more preferred —V is selected from hydrogen and methyl, especially hydrogen. Also more preferred is —$CR^2_2$—$CR^2_2$—$NH_2$.

The —$R^2$ moieties are each independently selected from hydrogen; halogen; unsubstituted or substituted alkyl, the alkyl portion having from about 1 to about 6 carbon atoms; substituted or unsubstituted aryl or heteroaryl; and carboxyl ate; or two —$R^2$ moieties are covalently bonded to form a substituted or unsubstituted alkyl, heteroalkyl, aryl or heteroaryl ring having from about 3 to about 8 atoms, preferably 3–6, in the ring, including from 0 to about 3 heteroatoms. It is preferred that no more than two —$R^2$ are other than hydrogen. Preferred —$R^2$ substituents other than hydrogen include unsubstituted and substituted $C_1$–$C_6$ alkyl and unsubstituted and substituted phenyl.

It is preferred that at least one —$R^2$ on the alpha carbon atom (the carbon atom bonded directly to the Y moiety) be a hydrogen. Preferred also is all —$R^2$ being selected from hydrogen and hydroxyalkyl having from about 1 to about 5 carbon atoms, more preferably 5-hydroxypentyl, 2-hydroxybutyl or hydroxymethyl, especially hydroxymethyl. Preferred also is all —$R^2$ being selected from hydrogen and aminoalkyl having from about 1 to about 5 carbon atoms, more preferably 2-aminopentyl, 2-aminobutyl, aminomethyl or aminoethyl, especially aminomethyl or aminoethyl. Preferred also is all —$R^2$ being selected from hydrogen and substituted or unsubstituted aryl, especially phenyl or methylphenyl. Preferred —$R^2$ moieties which are aryls include phenyl, naphthyl, and substituted phenyl or naphthyl; most preferred being substituted or unsubstituted phenyl. Preferred —$R^2$ moieties which are arylalkyls are substituted, or preferably, unsubstituted. Preferred —$R^2$ moieties which are substituted arylalkyls are those where the substituent groups are independently selected from $C_1$–$C_4$ alkyl, $C_1$–$C_4$ alkoxy, halogen, hydroxy, amino, hydrogen and carboxy groups. Preferred also is all —$R^2$ being selected from hydrogen and alkyl having from about 1 to about 5 carbon atoms (especially methyl). Also preferred is at most only one —$R^2$ being other than hydrogen. Also preferred is all —$R^2$ being hydrogen.

Particularly preferred is where both —$R^2$ on the alpha carbon atom are hydrogen and both —$R^2$ on the beta carbon atom (the carbon atom bonded directly to the alpha carbon atom) are unsubstituted or substituted alkyl or are covalently bonded to form a substituted or unsubstituted alkyl or heteroalkyl ring having from about 3 to about 8 atoms, including from 0 to about 3 heteroatoms, in the ring. As used herein, "heteroatoms" means atoms other than carbon that can covalently bond to at least two other atoms and become part of a stable ring structure. Preferred heteroatoms are N, O and S. More preferred —$R^2$ on the beta carbon atom are unsubstituted or substituted $C_1$–$C_6$ alkyl, more preferably $C_1$–$C_4$ alkyl, more preferably still $C_1$–$C_2$ alkyl. Also preferred are the two —$R^2$ moieties on the beta carbon atom being covalently bonded to form a substituted or unsubstituted alkyl ring having from about 3 to about 6 carbon atoms, more preferably 3 or 4 or 5 carbon atoms in the ring. Preferred —$R^2$ alkyl moieties on the beta carbon atom are saturated or unsaturated having a single double or triple bond, more preferred is that both —$R^2$ on the beta carbon be unsubstituted or substituted alkanyl or covalently bonded to form an unsubstituted or substituted alkanyl ring. Preferred substituents of the —$R^2$ alkyl moieties on the beta carbon are hydroxy, amino, thiol and carboxylate, especially hydroxy and amino. More preferred is that all —$R^2$ alkyl moieties on the beta carbon being unsubstituted. More preferred still is that both —$R^2$ on the beta carbon atom are methyl or ethyl, especially methyl.

In structure (1) the —R moiety is a $C_1$–$C_4$ alkyl moiety which may be straight, branched or cyclic chain and may be saturated, monounsaturated, or polyunsaturated, substituted or unsubstituted.

Preferred —R moieties are straight and branched chain alkanyl, straight and branched chain monounsaturated alkyl, straight and branched chain diunsaturated alkyl, and straight and branched chain triunsaturated alkyl. More preferred —R moieties are mono or diunsaturated or saturated, $C_6$–$C_{24}$ straight or branched chain alkyls. Also more preferred are $C_5$–$C_{11}$ straight chain alkyls, especially $C_7$–$C_{10}$ straight chain alkanyls. Even more preferred are mono or diunsaturated alkenyls, or $C_6$–$C_{24}$ straight chain alkenyls. Further preferred are monounsaturated cis-double bond $C_{11}$–$C_{23}$ straight chain alkenyls. Even further preferred is monounsaturated cis-double bond $C_{13}$–$C_{23}$ straight chain alkenyls. Most preferred —R is 9-Z-octadecenyl. Such preferred —R moieties are preferably unsubstituted.

Other preferred —R moieties are arylalkyls having a $C_1$–$C_{12}$, more preferably $C_1$–$C_6$, most preferably $C_1$–$C_2$, alkyl portion which is preferably straight chain and also preferably alkanyl. The aryl portion is preferably unsubstituted or substituted phenyl. Preferred substituents include halogen, nitro, cyano, phenyl, benzyl, benzyloxy, trifluoromethyl, formylamino, $C_1$–$C_6$ alkoxy and $C_1$–$C_4$ alkyl.

Preferred —R groups are as follows. For the methods of the present invention which use phenylacetic acid amide or thioamide derivatives, particularly the beta-aminoethoxy-substituted compounds having the general structure:

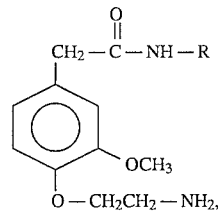

the preferred —R groups are selected from n-hexanyl, n-heptanyl, n-octanyl, n-nonanyl, n-decanyl, n-undecanyl, n-dodecanyl, n-tridecanyl, n-tetradecanyl, tetradecenyl, pentadecenyl, hexadecenyl, heptadecenyl, octadecenyl, nonadecenyl, eicosenyl, docosenyl, octadecadienyl, nonadecadienyl, eicosadienyl, octadecatrienyl, eicosatrienyl, eicosatetraenyl, octadecynyl, nonadecynyl, eicosynyl, and docosynyl. More preferred —R groups are selected from n-octanyl; n-nonanyl; n-decanyl; 9E- or 9Z-tetradecenyl; 9E- or Z-hexadecenyl; 9E- or 9Z-octadecenyl; 6E- or 6Z-octadecenyl; 11E-or 11Z-octadecenyl; 10E- or 10Z-nonadecenyl; 13E- or 13Z-docosenyl; 9-methylene-1-octadecanyl, 9Z; 12Z-octadecadienyl; 9E, 12E-octadecadienyl; 9Z, 12E-octadecadienyl; 9Z, 11E-octadecadienyl; 10E, 13E-nonadecadienyl; 11E, 14Z-eicosadienyl; 9Z, 12Z, 15Z-octadecatrienyl; 6Z, 9Z, 12Z-octadecatrienul; 11Z, 14Z, 17Z-eicosatrienyl; 5Z, 8Z, 11Z, 14Z-eicosatetraenyl; and 9-octadecynyl. Most preferred —R groups are n-octanyl, n-nonanyl, and 9Z-octadecenyl.

For the compounds of the present invention which are vanillylamide or vanillylthioamide derivatives, particularly the beta-aminoethoxy-substituted compounds having the general structure:

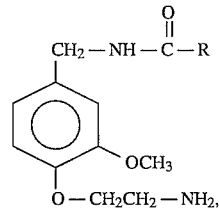

the preferred —R groups are selected from n-hexanyl, n-heptanyl, n-octanyl, n-nonanyl, n-decanyl, n-undecanyl, n-dodecanyl, n-tridecanyl, tridecenyl, tetradecenyl, pentadecenyl, hexadecenyl, heptadecenyl, octadecenyl, nonadecenyl, eicosenyl, docosenyl, heptadecadienyl, octadecadienyl, nonadecadienyl, eicosadienyl, heptadecatrienyl, octadecatrienyl, nonadecatrienyl, eicosatrienyl, nonadecatetraenyl, heptadecynyl, octadecynyl, nonadecynyl, and eicosynyl. More preferred —R groups are selected from n-heptanyl; n-octanyl; n-nonanyl; 8E- or 8Z-tridecenyl; 8E- or 8Z-pentadecenyl; 8E- or 8Z-heptadecenyl; 5E- or 5Z-heptadecenyl; 10E- or 10Z-heptadecenyl; 9E- or 9Z-octadecenyl; 12E- or 12Z-nonadecenyl; 8-methylene-1-heptadecanyl; 8Z, 11Z-heptadecadienyl; 8E, 11E-heptadecadienyl; 8Z, 11E-heptadecadienyl; 8Z, 10E-heptadecadienyl; 9E, 12E-octadecadienyl; 10E, 13E-nonadecadienyl; 8Z, 11Z, 14Z-heptadecatrienyl; 5Z, 8Z, 11Z-heptadecatrienyl; 10Z, 13Z, 16Z-nonadecatrienyl; 4Z, 7Z, 10Z, 13Z-nonadecatetraenyl; and 8-heptadecynyl. Most preferred —R groups are n-heptanyl, n-octanyl and 8Z-heptadecenyl (i.e., oleoyl amide).

The —R alkyl groups may be substituted or, preferably, unsubstituted. Preferred substituents are selected from the group consisting of halogen, hydroxy, amino, aryl, carboxylate, and —$OR^3$ wherein —$R^3$ is an unsubstituted alkyl group having from about 1 to about 3 carbon atoms (especially methoxy and ethoxy). It is preferred that substituted alkyl groups be mono-, di- or trisubstituted, most preferably monosubstituted.

The term "pharmaceutically-acceptable salts and amides", as used herein, means the compounds in their salt or amide form which have the same general pharmacological properties as the basic amino form from which they are derived, and which are acceptable from a toxicity viewpoint. Pharmaceutically-acceptable salts include ammonium salts derived from inorganic acids (e.g., HCl, HBr, $NAHSO_4$, $H_2CO_3$), and ammonium carboxylic acid salts derived from organic carboxylic acids (e.g., acetic acid; lactic acid; gluconic acid; citric acid; glucuronic acid; galacturonic acid; fumaric acid; gentisic acid; lactobionic acid; benzoic acid). Pharmaceutically-acceptable amides include those derived from organic carboxylic acids (e.g., acetic acid amides) including amino acids (e.g., glycine amides). Preferred are the ammonium carboxylic acid salts derived from organic carboxylic acids, especially the acetate and lactate salts.

Preferred compounds useful in the methods of the present invention include 8-methyl-N-vanillyl-6-nonenamide; N-vanillylnonanamide; N-vanillyl-9-octadecenamide; N-((4-(2-aminoethoxy)-3-methoxyphenyl)-methyl)-9Z-octadecenamide; N-((4-(2-aminoethoxy)-3-methoxyphenyl)-methyl)-nonanamide; N-((4-(2-methyl-2-aminopropoxy)-3-methoxyphenyl)-methyl)-nonanamide; N-((4-(2-methyl-2-aminopropoxy)-3-methoxyphenyl)-methyl)-9Z-octadecenamide; N-((4-(2-amino-3-methylbutoxy)-3-methoxyphenyl)-methyl)-9Z-octadecenamide; N-((4-(1-amino-1-cyclopropylmethoxy)-3-methoxyphenyl)-methyl)-9Z-octadecenamide; N-((4-(1-amino-1-cyclopropylmethoxy)-3-methoxy)phenyl)methyl)-9Z-octadecenamide; N-(9Z-octadecenyl)-4-(2-amino-2-methylpropoxy)-3-methoxyphenylacetamide; N-(9Z-octadecenyl)-4-(2-aminoethoxy)-3-methoxyphenylacetamide; N-octanyl-4-(2-aminoethoxy)-3-methoxyphenylacetamide; N-((4-(2-amino-3-hydroxypropoxy)-3-methoxyphenyl)-methyl)-9Z-octadecenamide; N-((4-(2-amino-2-carboxyethoxy)-3-methoxyphenyl)-methyl)-9Z-octadecenamide; and the pharmaceutically-acceptable salts and amides thereof. More preferred compounds useful in the methods of the present invention include 8-methyl-N-vanillyl-6-nonenamide; N-vanillylnonanamide; N-vanillyl-9-octadecenamide; N-((4-(2-aminoethoxy)-3-methoxyphenyl)-methyl)- 9Z-octadecenamide; N-(9Z-octadecenyl)-4-(2-aminoethoxy)-3-methoxyphenylacetamide; N-((4-(2-aminoethoxy)-3-methoxyphenyl)-methyl)-nonanamide; N-((4-(2-methyl-2-aminopropoxy)-3-methoxyphenyl)-methyl)-nonanamide; N-((4-(2-methyl-2-aminopropoxy)-3-methoxyphenyl)-methyl)-9Z-octadecenamide; N-(9Z-octadecenyl)-4-(2-amino-2-methylpropoxy)-3-methoxyphenylacetamide and the pharmaceutically-acceptable salts and amides thereof.

As noted hereinbefore, capsaicin and a wide variety of other substituted phenyl compounds are known to have analgesic activity. Heretofore, however, the capsaicinoids and other vanilloid compounds have not been shown to have an effect on herpes simplex infections. Surprisingly, natural and synthetic vanilloid compounds of the present invention are efficacious to help prevent and/or treat recurrent herpes simplex infections.

Specific pharmaceutical compositions useful in this invention are described in the following U.S. Pat. Nos., all incorporated by reference herein: U.S. Pat. Nos. 4,401,663, Buckwalter, et al, issued Aug. 30, 1983; 4,424,205, LaHann, et al, issued Jan. 31, 1984; 4,443,473, Buckwalter, et al, issued Apr. 12, 1984; 4,493,848, LaHann, et al, issued Jan. 15, 1985. Representative pharmaceutical compositions useful in the methods of the present invention are provided in the non-limiting Examples provided hereinafter. Such pharmaceutical compositions preferably comprise one or more of the vanilloid compounds and a pharmaceutically acceptable carrier.

The term "pharmaceutically-acceptable carrier", as used herein, means one or more compatible solid or liquid filler diluents or encapsulating substances which are suitable for administration to a human or lower animal. The term "compatible", as used herein, means that the components of a pharmaceutical carrier are capable of being commingled with the vanilloid compounds and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

The pharmaceutically-acceptable carrier employed in the methods of the present invention is used at a concentration sufficient to provide a practical size to dosage relationship. The pharmaceutically-acceptable carriers, in total, may comprise from about 50% to about 99.99% by weight of the pharmaceutical compositions of the present invention, preferably from about 90% to about 99.9%, and more preferably from about 95% to about 99.5%.

Total single dosages of the vanilloid compounds present in pharmaceutical compositions useful herein are generally from about 1 ug to about 1 g. Preferred single dosages are from about 10 ug to about 100 mg; more preferred are from about 100 ug to about 50 mg; and most preferred are from about 1 mg to about 10 mg.

The choice of a pharmaceutically-acceptable carrier to be used in conjunction with the compounds of the present invention is largely determined by the way the compound is to be administered. Such methods include parenteral (especially subcutaneous), oral and topical. As used herein, "administered topically" means placing the compounds in contact with the skin, mucous membrane, or body cavity. It thus includes epidermal, intraoral, intranasal, intravaginal, intraanal, intrauretheral, intraaural, and extraocular administration. The preferred methods of the present invention involve topical administration of the vanilloid compounds. Suitable pharmaceutically-acceptable carriers for topical application include those suited for use in lotions, creams, solutions, gels, tapes and the like.

Suitable carriers for topical administration preferably remain in place on the skin as a continuous film and resist being washed off easily by perspiration or by immersion in water. Generally, the carrier is either organic in nature or an aqueous emulsion and capable of having the vanilloid compound dispersed or dissolved therein. The carrier may include pharmaceutically-acceptable emollients, skin penetration enhancers, coloring agents, fragrances, emulsifiers, thickening agents, and solvents. A more detailed description of such forms follows:

1. Lotions

The lotions can comprise an effective amount (preferably from about 0.001% to about 5%, more preferably from about 0.1% to about 1%) of a vanilloid compound; from 1% to 50%, preferably from 3% to 15%, of an emollient; the balance being water, a $C_2$ or $C_3$ alcohol, or a mixture of water and the alcohol. Several emollients are known. Examples of such emollients are as follows:

a. Hydrocarbon oils and waxes. Examples are mineral oil, petrolatum, paraffin, ceresin, ozokerite, microcrystalline wax, polyethylene, and perhydrosqualene.

b. Silicone oils, such as dimethylpolysiloxanes, methylphenylpolysiloxanes, water-soluble and alcohol-soluble silcone-glycol copolymers.

c. Triglyceride fats and oils such as those derived from vegetable, animal and marine sources. Examples include castor oil, safflower oil, cotton seed oil, corn oil, olive oil, cod liver oil, almond oil, avocado oil, palm oil, sesame oil, and soybean oil.

d. Acetoglyceride esters, such as acetylated monoglycerides.

e. Ethoxylated glycerides, such as ethoxylated glyceryl monostearate.

f. Alkyl esters of fatty acids having 10 to 20 carbon atoms. Methyl, isopropyl and butyl esters of fatty acids are useful herein. Examples include hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl actate.

g. Alkenyl esters of fatty acids having 10 to 20 carbon atoms. Examples thereof include oleyl myristate, oleyl stearate, and oleyl oleate.

h. Fatty acids having 9 to 22 carbon atoms. Suitable examples include pelargonic, lauric, myristic, palmitic, stearic, isostearic, hydroxystearic, oleic, inoleic, ricinoleic, arachidonic, behenic, and erucic acids.

i. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

j. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

k. Ether-esters such as fatty acid esters of ethoxylated fatty alcohol s.

l. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

m. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M. W. 200–6000), methoxy polyethylene glycols 350, 550,750, 2000, 5000, poly[ethylene oxide] homopolymers (M. W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol) $C_{15}$–$C_{18}$ vicinal glycol, and polyoxypropylene derivates of trimethylolpropane are examples thereof.

n. Polyhydric alcohol esters. Ethylene glycol mono- and di-fatty acid esters, diethylene glycol mono- and di-fatty acid esters, polyethylene glycol (M. W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

o. Wax esters such as beeswax, spermaceti, myristyl myristate, stearyl stearate.

p. Beeswax derivatives, e.g., polyoxyethylene sorbitol beeswax. These are reaction products of beeswax with ethoxylated sorbitol of varying ethylene oxide content, forming a mixture of ether-esters.

q. Vegetable waxes including carnauba and candelilla waxes.

r. Phospholipids such as lecithin and derivatives.

s. Sterols. Cholesterol, cholesterol fatty acid esters are examples thereof.

t. Amides such as fatty acid amides, ethoxylated fatty acid amides, solid fatty acid alkanolamides.

The lotions further preferably comprise from 1% to 10%, more preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, an alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound of the present invention is dissolved in the mixture. Conventional optional components can be included. One such additive is a thickening agent at a level from 1% to 10% of the composition. Examples of suitable thickening agents include: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

2. Creams

The creams comprise an effective amount (preferably from about 0.001% to about 5%, more preferably from about 0.1% to about 1%) of a vanilloid compound; from 5% to 50%, preferably from 10% to 25%, of an emollient; the balance being water. The emollients above described can also be used in the cream compositions. Optionally the cream form contains a suitable emulsifier, as previously described. When an emulsifier is included, it is in the composition at a level from 3% to 50%, preferably from 5% to 20%.

3. Solutions

The solution form comprises an effective amount (preferably from about 0.001% to about 5%, more preferably from about 0.1% to about 1%) of a vanilloid compound; the balance being water and/or a suitable organic solvent. Suitable organic materials useful as the solvent or a part of a solvent system are as follows: propylene glycol, polyethylene glycol (M. W. 200–600), polypropylene glycol (M. W. 425–2025), glycerine, sorbitol esters, 1,2,6-hexanetriol, ethanol, isopropanol, diethyl tartrate, butanediol, and mixtures thereof. Such solvent systems can also contain water.

These compositions in solution form can be applied to the skin as is, or else can be formulated into an aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Gel compositions can be formulated by simply admixing a suitable thickening agent to the previously described solution compositions. Examples of suitable thickening agents have been previously described with respect to the lotions.

The gelled compositions comprise an effective amount (preferably from about 0.001% to about 5%, more preferably from about 0.1% to about 1%) of a vanilloid compound; from 5% to 75%, preferably from 10% to 50%, of an organic solvent as previously described; from 0.5% to 20%, preferably from 1% to 10% of the thickening agent; the balance being water.

5. Solids

Compositions of solid forms have use as stick-type compositions intended for application to the lips or other parts of the body. Such compositions comprise an effective amount (preferably from about 0.001% to about 5%, more preferably from about 0.1% to about 1%) of a vanilloid compound, and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

6. Genital Formulations

Compositions used in the present invention can be administered in a wide variety of vehicles, especially in the genital region. In addition to general skin treatment, infections in the genital area can be treated using vaginal, anal or uretheral suppositories; vaginal pessaries; vaginal or rectal tablets or inserts; catamenial and non-catamenial tampons; ointments; enemas; cones; emulsions; and douches.

Additives commonly found in topical compositions such as preservatives, e.g., methyl and ethyl-paraben, dyes and perfume can be included in any of the previously described topical compositions.

METHODS OF TREATING HERPES SIMPLEX INFECTIONS

The present invention involves methods of treating herpes simplex infections, including methods of alleviating signs and symptoms associated with herpetic vesicular eruptions and the attendant pain of herpes simplex lesions. The methods of the present invention may be useful for preventing recurrent herpes simplex infections and/or for relieving the symptoms associated with herpes simplex vesicular eruptions.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician. Daily dosages can range from about 0.01 mg/kg of body weight to about 5 mg/kg of body weight. Preferred daily dosages are from about 0.1 to about 2 mg/kg of body weight. Up to about 6 single dosages per day may be administered.

Topical administration can be used by directly laying on or spreading a safe and effective amount of a vanilloid composition on epidermal or epithelial tissue, including outer skin and oral, anal, vaginal, gingival, and nasal tissue. The amount of the pharmaceutical composition to be topically administered may vary from about 1 mg/cm$^2$ to about 20 mg/cm$^2$, and if a patch is worn over the affected area possibly higher amounts, depending upon such factors as the sensitivity, type and location of tissue to be treated, the composition and carrier to be administered, and the particular compound to be administered.

An animal model which can be used to demonstrate the use of vanilloids for the prevention or treatment of herpes simplex infections is disclosed in Stanberry, L. R., R. L. Burke and M. G. Myers, "Herpes Simplex Virus Glycoprotein Treatment of Recurrent Genital Herpes", *The Journal of Infectious Diseases*, Vol. 157, (1988), pp. 156–163; and Stanberry, L. R., S. Kit and M. G. Myers, "Thymidine Kinase-deficient Herpes Simplex Virus Type 2 Genital Infection in Guinea Pigs", *Journal of Virology*, Vol. 55, (1985), pp. 322–328.

EXAMPLE I

Female Hartley guinea pigs (300–350 g) are randomized into groups of 12. A mixture of Tween®, EtOH and 0.9% NaCl in distilled water is made to obtain the following concentrations (v/v):

10% Tween® 80

10% EtOH (ethanol)

80% 0.9% NaCl in distilled $H_2O$

The ethanol/Tween®/saline (ETS) vehicle is mixed with capsaicin to obtain a concentration of capsaicin of about 1.0%. Capsaicin is administered intravaginally in a 100 microliter volume of the (ETS) vehicle.

The guinea pigs are intravaginally inoculated with 5.0 log pfu HSV-II, MS strain, following capsaicin administration. The virologic course of primary infection 1–10 days post inoculation is assessed by determining the titer of virus in secretions collected by swabbing the vagina daily. The clinical course of primary infection is assessed, along with the incidence and duration of urinary retention, hindlimb paralysis, and the incidence of death occurring within 14 days of viral challenge. The frequency and severity of recurrent disease is determined by daily examination of the guinea pig after recovery from the primary infection of days 15–21 through day 100. Animals treated with capsaicin show zero or few lesions, whereas the untreated animals show numerous lesions. Similar results are obtained using a 1.0% concentration of N-vanillylnonanamide in the ETS vehicle.

Similar results are also obtained using a 1.0% concentration of N-((4-2-aminoethoxy)-3-methoxyphenyl)-methyl)-9Z-octadeccenamide in a vehicle consisting of 10% EtOH, 10% Tween® 80, and 80% of an aqueous buffer solution consisting of acetic acid (6 g/l) and sodium hydroxide (2 g/l) in distilled water.

EXAMPLE II

Synthesis of N-((4-(2-aminoethoxy)-3-methoxyphenyl)-methyl)-9 Z-octadecenamide by the Phthalimide Synthesis Method (a) Synthesis of N-((4-(2-bromoethoxy)-3-methoxyphenyl)methyl)-9Z-octadecenamide:

(I)

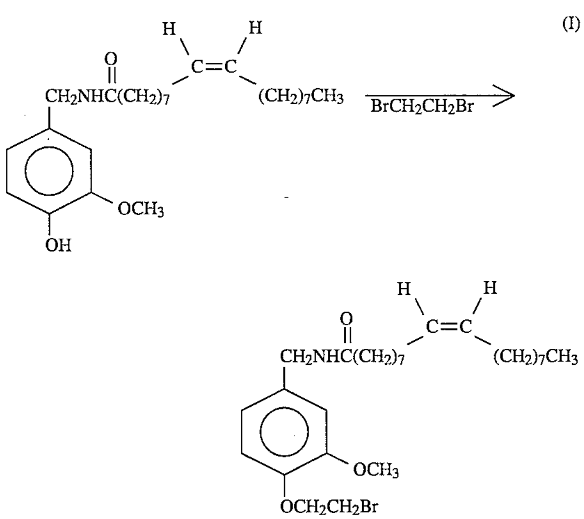

N-vanillyloleamide (100 gm, 0.24 mole; which is prepared as described in U.S. Pat. No. 4,493,848 to LaHann and Buckwalter, issued Jan. 15, 1985), 1,2-dibromoethane (500 ml), 40% KOH (165 ml) and 40% tetrabutylammonium hydroxide (15 ml) are combined in a 2 L flask equipped with a thermometer, mechanical stirrer and reflux condenser, and the solution is heated to 55° C. The disappearance of starting material is monitored by TLC (6% acetone/$CH_2Cl_2$). After the reaction is completed (typically after reacting overnight), the solution is diluted with $CHCl_3$ (500 ml), washed three times with water and the aqueous washings are then combined and extracted once with $CHCl_3$ (250 ml). The organic phases are combined, washed with 10% $H_3PO_4$ (250 ml), saturated $NaHCO_3$ (250 ml), brine, then dried ($MgSO_4$) and filtered. The volume is reduced to less than 500 ml by vacuum distillation and the liquid is then transferred to a 4-L flask. After cooling to approximately 10° C., $Et_2O$ (2 L) is added and the flask is cooled in an ice bath. A white precipitate forms and additional $Et_2O$ is added to make a volume of 4 l. The thick amorphous solid is filtered, washed with $Et_2O$, dried and used without further purification. Mp=96°–97° C. $^1H$ NMR ($CDCl_3$) (ppm): 6.8 (s, 3H), 5.9 (m, 1H), 5.3 (t, 2H J=5 Hz), 4.3 (m, 4H), 3.8 (s, 3H), 3.6 (t, 2H, J=6.5 Hz), 2.3–2.1 (m, 4H), 2.0–1.5 (m, 2H), 1.2 (s, 22H), 0.85 (t, 3H). $^{13}C$ NMR ($CDCl_3$) (ppm): 14.0, 22.5, 25.6, 27.0, 29.1, 31.7, 36.5, 43.0, 55.8, 69.3, 111.9, 115.0, 119.8, 129.5, 132.8, 146.5, 149.8, 172.8.

(b) Synthesis of N-((4-(2-phthalimidoethoxy)-3-methoxyphenyl)-methyl)-9Z-octadecenamide:

(I)

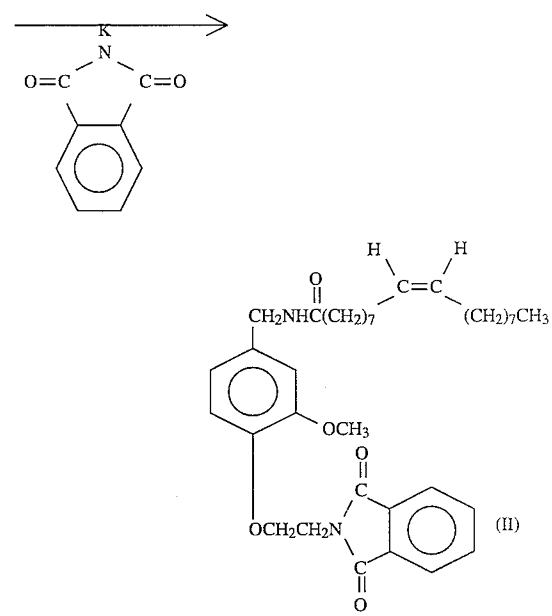

(II)

N-((4-(2-bromoethoxy)-3-methoxyphenyl)-methyl)-9Z-octadecenamide (615.5 gm, 1.17 moles) and DMF are combined in a 5 L flask equipped with a mechanical stirrer and a thermometer. The mixture is stirred and heated to 55° C. Once the solution becomes homogeneous, potassium phthalimide (270.0 gm, 1.47 mole) is added and the solution is maintained at 55° C. with good stirring. After ca. 10 minutes the reaction solution becomes homogeneous. Precipitation of a white solid then begins and the reaction is allowed to stir overnight at 55° C. TLC (acetone/dichloromethane 6:94) indicates when the starting material has been consumed. The reaction solution is divided into three equal volumes and each is worked up as follows: The solution is poured into a 4 L beaker and then diluted with water to the 3500 mL mark. After standing for ca. 15 minutes the solution is divided again into two equal parts, each of which is diluted to 3500 mL with water. The white precipitate is removed by filtration and washed several times with water. The three portions are combined and dried in a vacuum oven at 90° C. for 12 hours to give 682.25 g (98%) of a fine powder. Mp 109.5°–111.0° C. $^1$H NMR (CDCl$_3$)(ppm): 7.8 (m, 4H), 6.8 (m, 3H), 5.8 (m, 1H), 5.3 (t, 2H), 4.3 (d, 2H), 4.2 (t, 2H), 4.1 (t, 2H), 3.7 (s, 3H), 2.2–2.0 (m, 4H), 1.6 (m, 2H), 1.2 (s, 22H), 0.9 (t, 3H). $^{13}$C NMR (CDCl$_3$)(ppm): 172.8, 167.9, 150.0, 147.1, 133.9, 132.5, 132.1, 129.7, 123.1, 120.0, 114.9, 112.0, 66.2, 55.7, 43.2, 37.1, 36.7, 31.8, 29.3, 27.1, 25.7, 22.6, 14.0. IR (cm$^{-1}$): 3300, 1775, 1715, 1635, 1265, 1230, 1145, 1035, 1025, 720, CI-DEP Mass spectrum (m/z): 591 (MH+).

(c) Synthesis of N-((4-(2-aminoethoxy)-3-methoxyphenyl-)methyl)-9Z-octadecenamide:

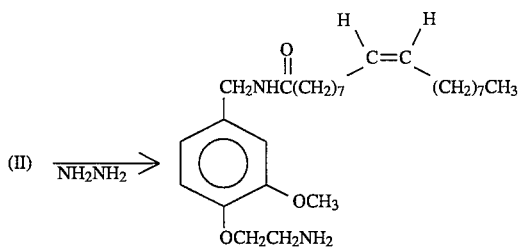

N-((4-(2-phthalimidoethoxy)-3-methoxyphenyl-methyl)-9Z-octadecenamide (250 gm, 0.424 mole) and ethanol (2500 mL) are combined in a 4 L beaker. The slurry is mechanically stirred and heated to 60° C. At ca. 45° C. the solution becomes homogeneous. 1-Hexene (20 mL) is added. Hydrazine hydrate (106 mL of a 64% aqueous solution) is then added. In ca. 5 minutes a white precipitate begins to form. During the 2 hour reaction time 500 mL of ethanol is added to the reaction to replenish that volume lost to evaporation. The reaction solution is then divided into three equal portions and each is worked up as follows: Methyl t-butyl ether (1.5 L) is used to transfer the slurry into a 4 L separatory funnel. Water (1 L) and 1N NaOH (500 mL) are added and the solution is thoroughly shaken. 50% NaOH (25 mL) is added and the solution is reshaken. The organic phase is then extracted twice with alkali using the same sequence, and washed with brine. The extract is dried over sodium sulfate and concentrated. The crude product is taken up in hot methyl t-butyl ether and allowed to crystallize. The crystals are filtered and dried in a vacuum desicator to give 124.87 g. A second crop of crystals, 40.82 g, is obtained to give 85% total yield. Mp 102°–106° C. $^1$H NMR (CDCl$_3$)(ppm): 6.7 (s, 3H), 6.1 (m, 1H), 5.3 (t, 2H), 4.3 (d, 2H), 3.9 (t, 3H), 3.8 (s, 3H), 3.0 (t, 2H), 2.5 (s, 2H), 2.1–1.6 (m, 4H), 1.5–1.2 (m, 2H), 1.2 (s, 22H), 0.9 (t, 3H). $^{13}$C NMR (CDCl$_3$) (ppm): 172.9, 149.3, 147.2, 131.8, 129.6, 119.7, 113.5, 111.4, 70.9, 55.5, 42.9, 40.9, 36.4, 31.6, 29.0, 26.9, 25.6, 22.4, 13.8. IR max (cm–$^1$): 3380, 3300, 1630, 1375, 1255, 1235, 1020, 800, 720 cm –1. CI-DEP Mass Spectrum (m/z): 461 (MH+).

While particular embodiments of the present invention have been described, it will be obvious to those skilled in the art that various changes and modifications to the compounds and compositions disclosed herein can be made without departing from the spirit and scope of the invention. It is intended to cover, in the appended claims, all such modifications that are within the scope of this invention.

What is claimed is:

1. A method of preventing vesicular eruptions (lesions) due to herpes simplex infections in a human comprising topically administering, prior to eruption of the lesions, to the human infected with a herpes simplex virus, a safe and effective amount of a compound, or the pharmaceutically acceptable salts and amides thereof, of the general structure:

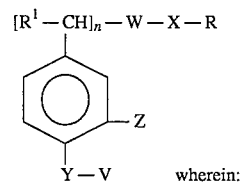

wherein:

a) n is 0 or 1.

b) —W—X— is —C(O)NH—, where either available bond of —W—X— is bonded to —R and the other bond is attached to the benzyl carbon atom or to the benzene ring;

c) —R$^1$ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms;

d) —Z is selected from the group consisting of —H, —OH, —OCH$_3$;

e) —Y— is selected from the group consisting of —O—, —S—, —NR$^4$—, —OC(O)—, —OSO$_3^-$—, and —OPO$_3^=$—, where —R$^4$ is selected from hydrogen and C$_1$–C$_4$ alkanyl;

f) —V is selected from the group consisting of —H, short chain alkyl, and —CR$^2_2$—CR$^2_2$—NH$_2$;

g) —R$^2$ moieties are independently selected from the group consisting of hydrogen; halogen; unsubstituted or substituted alkyl, the alkyl portion having from about 1 to about 6 carbon atoms; substituted or unsubstituted aryl; and carboxylate; or two —R$^2$ moieties are covalently bonded to form a substituted or unsubstituted alkyl, heteroalkyl, aryl or heteroaryl ring having from about 3 to about 8 atoms in the ring including from 0 to about 3 heteroatoms; and h) —R is C$_1$–C$_{24}$ alkyl.

2. The method of claim 1 wherein n is 1; —W—X— is selected from the group consisting of —C(O)NH—, —C(S)NH—, —NHC(O)NH—, —NHC(S)NH—, and —S(O)$_2$NH—; —R$^1$ is selected from the group consisting of —H, —OH, and —CH$_3$; —Y— is selected from the group consisting of —O—, —S—, and —NH—; and —R is selected from the group consisting of unsubstituted, saturated or mono—or diunsaturated, C$_6$–C$_{24}$ straight or branched chain alkyl, or arylalkyl having a C$_1$–C$_{12}$ alkyl portion.

3. The method of claim 2 wherein —W—X— is selected from the group consisting of —C(O)NH— and —C(S)NH—; —Y— is selected from the group consisting of —O—, and —S—; no more than two —R$^2$'s are other than hydrogen; and —R is saturated or mono- or di-unsaturated with double bonds C$_6$–C$_{24}$ straight chain alkyl.

4. The method of claim 3 wherein —W—X— is —C(O)NH—; —Y— is —O—, and —Z is selected from the group consisting of —OCH$_3$ and —OH.

5. The method of claim 4 wherein —R$^1$ is —H; and —R is a mono-unsaturated, cis double bond, C$_{11}$–C$_{23}$ straight chain alkenyl.

6. The method of claim 5 wherein —V is selected from the group consisting of —H, and —CH$_3$.

7. The method of claim 6 wherein said compound is trans-8-methyl-N-vanillyl-6-nonenamide.

8. The method of claim 6 wherein said compound is N-vanillylnonanamide.

9. The method of claim 4, wherein —V is —CR$^2_2$—CR$^2_2$—NH$_2$; and —Z is OCH$_3$.

10. The method of claim 9 wherein both —R$^2$ on the beta carbon are methyl, ethyl or are bonded to form cyclopropyl, cyclobutyl or cyclopentyl; and —R is selected from the group consisting of unsubstituted, saturated or mono— unsaturated, C$_6$–C$_{24}$ straight chain alkyl.

11. The method of claim 9 wherein both —R$^2$ on the beta carbon are methyl.

12. The method of claim 9 wherein all —R$^2$ are —H.

13. The method of claim 9 wherein —R is selected from a mono-unsaturated, cis-double bond, C$_{17}$–C$_{23}$ straight chain alkenyl, and a saturated, C$_7$–C$_{10}$ straight chain alkanyl.

14. The method of claim 9 wherein all —R$^{2'}$s are selected from hydrogen, unsubstituted or substituted C$_1$–C$_6$ alkyl, unsubstituted or substituted phenyl, and two —R$^{2'}$s being bonded to 15. The method of claim 1 wherein the compound has the general structure:

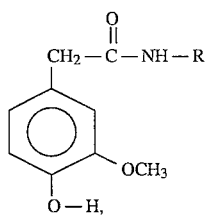

wherein —R is mono or diunsaturated or saturated C$_6$–C$_{24}$ alkyl.

16. The method of claim 15, wherein —R is monounsaturated cis-double bond C$_{11}$–C$_{23}$ straight-chain alkenyl.

17. The method of claim 1 wherein the compound has the general structure:

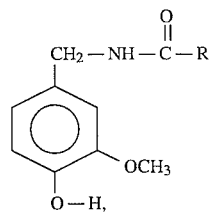

wherein —R is mono- or diunsaturated or saturated C$_6$–C$_{24}$ alkyl.

18. The method of claim 17, wherein —R is monounsaturated cis—double bond C$_{11}$–C$_{23}$ straight-chain alkenyl.

19. The method of claim 15 or 17 wherein —R is C$_6$–C$_{11}$ straight-chain alkyl.

20. The method of any of claims 1, 4, 6, 7, 8, 15, 16, 17 or 18 wherein from about 1 mg/cm$^2$ to about 20 mg/cm$^2$ of said compound is administered topically.

21. The method of any of claims 1, 6, 15, 16, 17 or 18 wherein from about 1 mg/cm$^2$ to about 20 mg/cm$^2$ of said compound is topically applied between herpes lesions outbreaks to prevent the recurrence of lesions.

22. The method of any of claims 1, 6, 15, 16, 17 or 18 wherein from about 1 mg/cm$^2$ to about 20 mg/cm$^2$ of said compound is topically applied to the genital region between genital herpes lesion outbreaks to prevent recurrence of lesions in the genital region.

23. The method of any of claims 1, 4, 6, 15, 16, 17 or 18 wherein said compound is used to prevent herpes simplex Type II lesions.

* * * * *

UNITED STATES PATENT AND TRADEMARK OFFICE
CERTIFICATE OF CORRECTION

PATENT NO. : 5,461,075
DATED : October 24, 1995
INVENTOR(S) : O'Neill, et. al.

It is certified that error appears in the above-indentified patent and that said Letters Patent is hereby corrected as shown below:

Column 19, line 18(fourth line of Claim 14), after "bonded to" insert --form a substituted or unsubstituted $C_3$-$C_6$ alkyl ring.--

Signed and Sealed this

Eighth Day of April, 1997

BRUCE LEHMAN

*Attest:*

*Attesting Officer*   *Commissioner of Patents and Trademarks*